US010213771B2

(12) United States Patent
Yang et al.

(10) Patent No.: US 10,213,771 B2
(45) Date of Patent: Feb. 26, 2019

(54) SCM-11 MOLECULAR SIEVE, PROCESS FOR PRODUCING SAME AND USE THEREOF (71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Weimin Yang, Shanghai (CN); Zhendong Wang, Shanghai (CN); Hongmin Sun, Shanghai (CN); Bin Zhang, Shanghai (CN); Yi Luo, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 185 days.

(21) Appl. No.: 15/347,117

(22) Filed: Nov. 9, 2016

(65) Prior Publication Data
US 2017/0128918 A1 May 11, 2017

(30) Foreign Application Priority Data

Nov. 9, 2015 (CN) .......................... 2015 1 0753651

(51) Int. Cl.
*C01B 39/48* (2006.01)
*B01J 29/04* (2006.01)
(Continued)

(52) U.S. Cl.
CPC ............. *B01J 29/047* (2013.01); *B01J 20/18* (2013.01); *B01J 29/86* (2013.01); *C01B 39/00* (2013.01);
(Continued)

(58) Field of Classification Search
CPC ......... C01B 39/48; C01B 39/06; C01B 39/08; C01B 39/12; B01J 29/70; B01J 20/18;
(Continued)

(56) References Cited

U.S. PATENT DOCUMENTS 2,882,244 A 4/1959 Milton
3,130,007 A 4/1964 Breck
(Continued)

FOREIGN PATENT DOCUMENTS

CN 85103247 A * 10/1986
CN 85103247 A 10/1986
(Continued)

*Primary Examiner* — David M Brunsman
(74) *Attorney, Agent, or Firm* — Novick, Kim & Lee, PLLC; Allen Xue (57) ABSTRACT The present invention relates to an SCM-11 molecular sieve, a process for producing same and use thereof. The molecular sieve has an empirical chemical composition as illustrated by the formula "the first oxide·the second oxide", wherein the ratio by molar of the first oxide to the second oxide is more than 2, the first oxide is silica, the second oxide is at least one selected from the group consisting of germanium dioxide, alumina, boron oxide, iron oxide, gallium oxide, titanium oxide, rare earth oxides, indium oxide and vanadium oxide. The molecular sieve has specific XRD pattern, and can be used as an adsorbent or a catalyst for converting an organic compound.

21 Claims, 2 Drawing Sheets (51) Int. Cl.
  *B01J 20/18* (2006.01)
  *B01J 29/86* (2006.01)
  *C01B 39/12* (2006.01)
  *C01B 39/00* (2006.01)
  *C07C 2/66* (2006.01)

(52) U.S. Cl.
  CPC .............. *C01B 39/12* (2013.01); *C01B 39/48* (2013.01); *C07C 2/66* (2013.01); *C01P 2002/72* (2013.01); *C07C 2529/04* (2013.01)

(58) Field of Classification Search
  CPC . B01J 29/047; B01J 29/86; B01J 29/87; B01J 29/88; B01J 29/89; C01P 2002/72
  See application file for complete search history.

(56) References Cited

U.S. PATENT DOCUMENTS

| | | | |
|---|---|---|---|
| 3,702,886 A | 11/1972 | Argauer et al. | |
| 4,390,457 A | 6/1983 | Klotz | |
| 4,410,501 A | 10/1983 | Taramasso et al. | |
| 6,080,382 A * | 6/2000 | Lee | B01D 53/8628 208/111.01 |
| 8,057,782 B2 * | 11/2011 | Miller | C01B 37/00 423/702 |
| 8,900,548 B2 * | 12/2014 | Burton | B01J 29/70 423/706 |
| 2011/0011810 A1 | 1/2011 | Lorgouilloux et al. | |
| 2011/0130579 A1 | 6/2011 | Müller et al. | |
| 2013/0095030 A1 | 4/2013 | Burton | |
| 2017/0128923 A1 * | 5/2017 | Yang | B01J 29/86 |
| 2018/0128924 A1 * | 5/2018 | Wu | G01S 19/14 |

FOREIGN PATENT DOCUMENTS

| | | |
|---|---|---|
| CN | 1245475 A | 2/2000 |
| CN | 101573182 A | 11/2009 |
| CN | 104445246 A | 3/2015 |
| CN | 104445247 A | 3/2015 |
| CN | 104445263 A | 3/2015 |
| CN | 104511271 A | 4/2015 |
| WO | 2008110526 A1 | 9/2008 |

* cited by examiner

SCM-11 MOLECULAR SIEVE, PROCESS FOR PRODUCING SAME AND USE THEREOF

TECHNICAL FIELD

The present invention relates to an SCM-11 molecular sieve, a process for producing same and use thereof.

BACKGROUND ART

In industry, porous inorganic materials have been widely used as catalysts and catalyst carriers. These porous materials generally include amorphous porous materials, crystalline molecular sieves and modified layered materials. Minute difference in the structure between any two materials may indicate significant difference in properties like catalytic performance and adsorbing ability therebetween, and further difference in available parameters used to characterize same, such as morphology, specific surface area or pore size.

The structure of a molecular sieve is specifically confirmed by the X-ray diffraction pattern (XRD), while the X-ray diffraction pattern (XRD) is determined by X-ray powder diffraction with a Cu—K α-ray source and a Ni filter. Different molecular sieves have different characterizing XRD patterns. Known molecular sieves, like A-Type Zeolite, Y-Type Zeolite, MCM-22 molecular sieve and so on, have their characterizing XRD patterns respectively.

At the same time, two molecular sieves, if sharing the same characterizing XRD pattern but comprising different combination of skeleton elements, will be identified as different molecular sieves.

For example, TS-1 molecular sieve (U.S. Pat. No. 4,410,501) and ZSM-5 molecular sieve (U.S. Pat. No. 3,702,886), share the same characterizing XRD pattern but comprise different combination of skeleton elements. Specifically, TS-1 molecular sieve comprises Si and Ti as the skeleton elements, exhibiting a catalytic oxidation ability, while ZSM-5 molecular sieve comprises Si and Al as the skeleton elements, exhibiting an acidic catalytic ability.

Further, two molecular sieves, if sharing the same characterizing XRD pattern and the same combination of skeleton elements but with different relative amounts of the skeleton elements, will be identified as different molecular sieves as well. For example, Zeolite X (U.S. Pat. No. 2,882,244) and Zeolite Y (U.S. Pat. No. 3,130,007), share the same characterizing XRD pattern and the same combination of skeleton elements (Si and Al), but with different relative amounts of Si and Al. Specifically, Zeolite X has a Si/Al molar ratio of less than 1.5, while Zeolite Y has a Si/Al molar ratio of greater than 1.5.

INVENTION SUMMARY

The present inventors, on the basis of the prior art, found a novel SCM-11 molecular sieve, and further identified beneficial properties for same.

Specifically, this invention relates to the following aspects.

1. An SCM-11 molecular sieve, having an empirical chemical composition as illustrated by the formula "the first oxide·the second oxide", wherein the first oxide is silica, the second oxide is at least two selected from the group consisting of germanium dioxide, alumina, boron oxide, iron oxide, gallium oxide, titanium oxide, rare earth oxides, indium oxide and vanadium oxide, more preferably a combination of germanium dioxide and at least one selected from the group consisting of alumina, boron oxide, iron oxide, gallium oxide, titanium oxide, rare earth oxides, indium oxide and vanadium oxide, more preferably a combination of germanium dioxide and at least one selected from the group consisting of alumina, boron oxide, titanium oxide and vanadium oxide, more preferably a combination of germanium dioxide and alumina, the ratio by molar of the first oxide to the second oxide is more than 2, preferably 3-1000, more preferably 4-400, more preferably 5-100, more preferably 5-50, most preferably the first oxide is silica, the second oxide is a combination of germanium dioxide and alumina, wherein $SiO_2/GeO_2>3$, $(SiO_2+GeO_2)/Al_2O_3>5$, and the molecular sieve has X ray diffraction pattern as substantially illustrated in the following table,

| $2\theta\ (°)\ ^{(a)}$ | d-spacing (Å) | Relative intensity ($I/I_0 \times 100$) |
| --- | --- | --- |
| 6.31 | 13.99 | vs |
| 7.20 | 12.27 | w-m |
| 7.97 | 11.09 | m-s |
| 9.43 | 9.37 | w |
| 12.63 | 7.00 | w-m |
| 18.05 | 4.91 | m |
| 22.98 | 3.87 | m-s |

$^{(a)} \pm 0.30°$.

2. The molecular sieve according to the aspect 1, wherein the X-ray diffraction pattern further includes X-ray diffraction peaks as substantially illustrated in the following table,

| $2\theta\ (°)\ ^{(a)}$ | d-spacing (Å) | Relative intensity ($I/I_0 \times 100$) |
| --- | --- | --- |
| 12.86 | 6.88 | w-m |
| 18.27 | 4.85 | w |
| 19.01 | 4.67 | s |
| 19.91 | 4.46 | w |
| 21.03 | 4.22 | m-s |
| 22.06 | 4.03 | w |
| 23.33 | 3.81 | w |
| 24.60 | 3.62 | m |
| 25.39 | 3.51 | m |
| 25.89 | 3.44 | w-m |
| 26.65 | 3.34 | m-s |
| 27.96 | 3.19 | w |

$^{(a)} \pm 0.30°$.

3. An SCM-11 molecular sieve, in the synthesized form having an empirical chemical composition as illustrated by the formula "the first oxide·the second oxide·the organic template·water", wherein the first oxide is silica, the second oxide is at least two selected from the group consisting of germanium dioxide, alumina, boron oxide, iron oxide, gallium oxide, titanium oxide, rare earth oxides, indium oxide and vanadium oxide, more preferably a combination of germanium dioxide and at least one selected from the group consisting of alumina, boron oxide, iron oxide, gallium oxide, titanium oxide, rare earth oxides, indium oxide and vanadium oxide, more preferably a combination of germanium dioxide and at least one selected from the group consisting of alumina, boron oxide, titanium oxide and vanadium oxide, more preferably a combination of germanium dioxide and alumina, the ratio by molar of the first oxide to the second oxide is more than 2, preferably 3-1000, more preferably 4-400, more preferably 5-100, more preferably 5-50, most preferably the first oxide is silica, the second oxide is a combination of germanium dioxide and alumina, wherein $SiO_2/GeO_2>3$, $(SiO_2+GeO_2)/Al_2O_3>5$, the ratio by weight of the organic template to the first oxide is 0.03-0.40, preferably 0.05-0.33, more preferably 0.06-0.30, more preferably 0.06-0.25, more preferably 0.07-0.19, the ratio by weight of water to the first oxide is 0-0.15, preferably 0.02-0.11, and the molecular sieve has X ray diffraction pattern as substantially illustrated in the following table,

| 2θ (°) [a] | d-spacing (Å) | Relative intensity ($I/I_0 \times 100$) |
|---|---|---|
| 6.32 | 13.97 | vs |
| 7.14 | 12.36 | s |
| 7.88 | 11.22 | vs |
| 9.33 | 9.47 | m |
| 12.63 | 7.00 | w-m |
| 18.05 | 4.91 | m-s |
| 23.02 | 3.86 | m |

[a] ±0.30°.

4. The molecular sieve according to the aspect 3, wherein the X-ray diffraction pattern further includes X-ray diffraction peaks as substantially illustrated in the following table,

| 2θ (°) [a] | d-spacing (Å) | Relative intensity ($I/I_0 \times 100$) |
|---|---|---|
| 6.87 | 12.86 | m-s |
| 14.25 | 6.21 | w-m |
| 18.67 | 4.75 | m-s |
| 19.71 | 4.50 | w-m |
| 20.72 | 4.28 | s |
| 21.60 | 4.11 | m |
| 24.33 | 3.66 | m |
| 25.21 | 3.53 | m-s |
| 25.57 | 3.48 | m |
| 26.12 | 3.41 | m |
| 26.47 | 3.36 | s |
| 27.62 | 3.23 | w |

[a] ±0.30°.

5. The molecular sieve according to anyone of the preceding aspects, wherein the molecular sieve has a specific surface area of 300-650 m²/g, preferably 350-550 m²/g, and a micropore volume of 0.06-0.30 cm³/g, preferably 0.08-0.26 cm³/g, more preferably 0.10-0.24 cm³/g, more preferably 0.12-0.22 cm³/g, more preferably 0.14-0.20 cm³/g.

6. The molecular sieve according to anyone of the preceding aspects, wherein the molecular sieve has a ring channel in the range of from 8-membered ring to 14-membered ring, preferably in the range of from 10-membered ring to 12-membered ring, and a pore size (by the Argon adsorption method) of 0.54-0.80 nm, preferably 0.58-0.74 nm.

7. The molecular sieve according to anyone of the preceding aspects, wherein there are significant signal peaks at the wave number of 384±10 and at the wave number of 487±10 in the UV Raman spectroscopy thereof.

8. A process for producing an SCM-11 molecular sieve, including a step of contacting under multiple step crystallization conditions a first oxide source, a second oxide source, an organic template, a fluorine source and water, to obtain a molecular sieve, and optionally, a step of calcining the obtained molecular sieve, wherein the first oxide source is a silicon source, the second oxide source is at least two selected from the group consisting of a germanium source, an aluminum source, a boron source, an iron source, a gallium source, a titanium source, a rare earth source, an indium source and a vanadium source, more preferably a combination of a germanium source and at least one selected from the group consisting of an aluminum source, a boron source, a gallium source, a titanium source, a rare earth source, an indium source and a vanadium source, more preferably a combination of a germanium source and at least one selected from the group consisting of an aluminum source, a boron source, a titanium source and a vanadium source, more preferably a combination of the germanium source and the aluminum source.

9. The process according to anyone of the preceding aspects, wherein the multiple step crystallization conditions at least include: crystallizing at 80-110 degrees Celsius for 8 hours to 2 days, and then at 120-160 degrees Celsius for 1-10 days, preferably firstly crystallizing at 80-110 degrees Celsius for 12-36 hours, and then at 120-135 degrees Celsius for 4-36 hours, finally at 140-160 degrees Celsius for 1-7 days, more preferably firstly crystallizing at 90-110 degrees Celsius for 12-36 hours, and then at 125-135 degrees Celsius for 4-36 hours, finally at 140-155 degrees Celsius for 1-5 days, more preferably firstly crystallizing at 110 degrees Celsius for 18-30 hours, and then at 130 degrees Celsius for 12-36 hours, finally at 150 degrees Celsius for 1.5-3 days.

10. The process according to anyone of the preceding aspects, wherein the silicon source is at least one selected from the group consisting of silicic acid, silica gel, silica sol, tetralkoxysilane and water glass, the germanium source is at least one selected from the group consisting of tetralkoxy germanium, germanium dioxide and germanium nitrate, the aluminum source is at least one selected from the group consisting of aluminum hydroxide, sodium aluminate, aluminum salts, aluminum alkoxides, kaolin and montmorillonite, the aluminum salts is at least one selected from the group consisting of aluminum sulfate, aluminum nitrate, aluminum carbonate, aluminum phosphate, aluminum chloride and alum, the aluminum alkoxides is at least one selected from the group consisting of aluminum isopropoxide, aluminum ethoxide and aluminum butoxide, the boron source is at least one selected from the group consisting of boric acid, borate salt, borax and diboron trioxide, the iron source is at least one selected from the group consisting of ferric nitrate, ferric chloride and iron oxide, the gallium source is at least one selected from the group consisting of gallium nitrate, gallium sulfate and gallium oxide, the titanium source is at least one selected from the group consisting of titanium tetralkoxide, titania and titanium nitrate, the rare earth source is at least one selected from the group consisting of lanthanum oxide, neodymium oxide, yttrium oxide, cerium oxide, lanthanum nitrate, neodymium nitrate, yttrium nitrate, and ceric ammonium sulfate, the indium source is at least one selected from the group consisting of indium chloride, indium nitrate and indium oxide, the vanadium source is at least one selected from the group consisting of vanadium chloride, ammonium metavanadate, sodium vanadate, vanadium dioxide, and vanadyl sulfate, the organic template is selected from a compound represented by the following formula (A), a quaternary ammonium salt thereof and a quaternary ammonium hydroxide thereof, preferably 4-dimethylamino pyridine, (A)

wherein $R_1$ and $R_2$ may be identical to or different from each other, each independently representing a $C_{1-8}$ alkyl, preferably a $C_{1-4}$ alkyl, more preferably a $C_{1-2}$ alkyl.

11. The process according to anyone of the preceding aspects, wherein the ratio by molar between the first oxide source (as the first oxide), the second oxide source (as the second oxide), the organic template, the fluorine source (as F) and water is 1:(0-0.5):(0.1-2.0):(0.1-2.0):(4-50), preferably 1: (0.001-⅓): (0.1-1.0): (0.1-1.0): (4-40), more preferably 1: (0.0025-0.25): (0.1-0.8): (0.1-1.0): (4-40), more preferably 1:(0.01-0.2):(0.1-0.6):(0.1-1.0):(5-30), more preferably 1:(0.02-0.2):(0.1-0.6):(0.1-1.0):(5-30).

12. A molecular sieve composition, comprising the molecular sieve according to anyone of the preceding aspects or a molecular sieve produced in line with the process according to anyone of the preceding aspects, and a binder.

13. Use of the molecular sieve according to anyone of the preceding aspects, a molecular sieve produced in line with the process according to anyone of the preceding aspects or the molecular sieve composition according to anyone of the preceding aspects as an adsorbent, an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst or an aromatic disproportionation catalyst.

TECHNICAL EFFECTS

According to the present invention, the SCM-11 molecular sieve is a novel molecular sieve having a structure that has never been identified in the field, which can be confirmed by at least its unique X-ray diffraction pattern.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims. Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

In the context of this specification, a molecular sieve, before any other material (for example, organic templates) than water and metal ions that has been filled into its pores during the production thereof is removed from the pores, is referred to as "precursor".

In the context of this specification, in the XRD data of the molecular sieve, w, m, s, vs indicate the intensity of a diffraction peak, with w referring to weak, m to medium, s to strong, vs to very strong, which has been well known in this field. In general, w represents a value of less than 20; m represents a value of 20-40; s represents a value of 40-70; vs represents a value of greater than 70.

In the context of this specification, the molecular sieve structure is confirmed by the X-ray diffraction pattern (XRD), while the X-ray diffraction pattern (XRD) is determined by X-ray powder diffraction with a Cu—K α-ray source and a Ni filter. Before determination, the crystalline state of the test sample is observed under scanning electron microscope (SEM), to confirm that there presents only one type of crystal therein, which indicates that the molecular sieve as the test sample presents as a pure phase, and then the XRD determination is conducted thereon, in order to ensure that there is no interfering peak of other crystal in the XRD pattern. In the context of this specification, by specific surface area, it refers to the total area per unit of mass of a sample, including the internal surface area and the external surface area. A non-porous material has only external surface area, like Portland cement or some clay mineral powder, while a porous material has an external surface area and an internal surface area, like asbestos fiber, diatomite or molecular sieves. In a porous material, the surface area of pores having a diameter of less than 2 nm is referred to as internal surface area, while the surface area obtained by subtracting the internal surface area from the total surface area is referred to as external surface area. The external surface area per unit of mass of a sample is referred to as external specific surface area.

In the context of this specification, by pore volume, it refers to the volume of pores per unit of mass of a porous material (e.g. a molecular sieve). By total pore volume, it refers to the volume of all pores (generally involving only pores having a pore diameter of less than 50 nm) per unit of mass of a molecular sieve. By micropore volume, it refers to the volume of all micropores (generally referred to pores having a pore diameter of less than 2 nm) per unit of mass of a molecular sieve.

The present invention relates to an SCM-11 molecular sieve. The SCM-11 molecular sieve is a novel molecular sieve having a structure that has never been identified in the field, which can be confirmed by at least its unique X-ray diffraction pattern.

According to the present invention, the SCM-11 molecular sieve may present without calcination (referred to as the synthesized form), or after calcined (referred to as the calcined form). If present in the synthesized form, the SCM-11 molecular sieve generally has an empirical chemical composition as illustrated by the formula "the first oxide·the second oxide·the organic template·water", if present in the calcined form or in the synthesized form, the SCM-11 molecular sieve may have an empirical chemical composition as illustrated by the formula "the first oxide·the second oxide". In the latter case, it is known that, a molecular sieve will sometimes (especially immediately after the production thereof) contain a certain amount of water, however, this invention does not specify or identify as to how much this amount may be, since the presence or absence of water will not substantially change the XRD pattern of the present molecular sieve. In this context, the empirical chemical composition actually represents an anhydrous chemical composition of this molecular sieve. Further, it is obvious that the empirical chemical composition represents the framework chemical composition of the molecular sieve.

According to the present invention, in the empirical chemical composition of the SCM-11 molecular sieve, the ratio by molar the first oxide to the second oxide is generally more than 2, preferably 3-1000, more preferably 4-400, more preferably 5-100, more preferably 5-50. According to the present invention, the first oxide is silica.

According to the present invention, the second oxide is at least two selected from the group consisting of germanium dioxide, alumina, boron oxide, iron oxide, gallium oxide, titanium oxide, rare earth oxides, indium oxide and vanadium oxide, more preferably a combination of germanium dioxide and at least one selected from the group consisting of alumina, boron oxide, iron oxide, gallium oxide, titanium oxide, rare earth oxides, indium oxide and vanadium oxide, more preferably a combination of germanium dioxide and at least one selected from the group consisting of alumina, boron oxide, titanium oxide and vanadium oxide, more preferably a combination of germanium dioxide and alumina.

According to one embodiment of the present invention, generally speaking, if multiple second oxides are used in combination, the ratio by molar between any two oxides is 1-99.6:99-0.4, preferably 33-99.5:67-0.5, more preferably 50-99:50-1, more preferably 60-99:40-1, more preferably 66-98:34-2, more preferably 66-97:34-3. Especially, if the second oxide is a combination of germanium dioxide and alumina, preferably Ge/Al=0.5-100, more preferably 1-50, more preferably 1.5-30, more preferably 2-20.

According to a preferred embodiment of the present invention, the first oxide is silica, the second oxide is a combination of germanium dioxide and alumina, wherein $SiO_2/GeO_2 > 3$, and $(SiO_2 + GeO_2)/Al_2O_3 > 5$.

According to the present invention, in the formula "the first oxide·the second oxide·the organic template·water", the ratio by weight of the organic template to the first oxide is 0.03-0.40, preferably 0.05-0.33, more preferably 0.06-0.30, more preferably 0.06-0.25, more preferably 0.07-0.19.

According to the present invention, in the formula "the first oxide·the second oxide·organic template·water", the ratio by weight of water to the first oxide is 0-0.15, preferably 0.02-0.11. According to the present invention, if present in the calcined form, the molecular sieve has X ray diffraction pattern as substantially illustrated in the following table,

| 2θ (°) [a] | d-spacing (Å) | Relative intensity ($I/I_0 \times 100$) |
|---|---|---|
| 6.31 | 14.03 ± 0.67 | vs |
| 7.20 | 12.29 ± 0.51 | w-m |
| 7.97 | 11.10 ± 0.42 | m-s |
| 9.43 | 9.38 ± 0.30 | w |
| 12.63 | 7.01 ± 0.17 | w-m |
| 18.05 | 4.91 ± 0.08 | m |
| 22.98 | 3.87 ± 0.05 | m-s |

[a] ±0.30°.

According to the present invention, if present in the calcined form, the X-ray diffraction pattern may further include X-ray diffraction peaks as substantially illustrated in the following table,

| 2θ (°) [a] | d-spacing (Å) | Relative intensity ($I/I_0 \times 100$) |
|---|---|---|
| 12.86 | 6.88 ± 0.16 | w-m |
| 18.27 | 4.85 ± 0.08 | w |
| 19.01 | 4.67 ± 0.07 | s |
| 19.91 | 4.46 ± 0.07 | w |
| 21.03 | 4.22 ± 0.06 | m-s |
| 22.06 | 4.03 ± 0.05 | w |
| 23.33 | 3.81 ± 0.05 | w |
| 24.60 | 3.62 ± 0.04 | m |
| 25.39 | 3.51 ± 0.04 | m |
| 25.89 | 3.44 ± 0.04 | w-m |
| 26.65 | 3.34 ± 0.04 | m-s |
| 27.96 | 3.19 ± 0.03 | w |

[a] ±0.30°.

According to the present invention, if present in the synthesized form, the molecular sieve has X ray diffraction pattern as substantially illustrated in the following table.

| 2θ (°) [a] | d-spacing (Å) | Relative intensity ($I/I_0 \times 100$) |
|---|---|---|
| 6.32 | 14.01 ± 0.66 | vs |
| 7.14 | 12.39 ± 0.52 | s |
| 7.88 | 11.23 ± 0.43 | vs |
| 9.33 | 9.48 ± 0.30 | m |
| 12.63 | 7.01 ± 0.17 | w-m |
| 18.05 | 4.91 ± 0.08 | m-s |
| 23.02 | 3.86 ± 0.05 | m |

[a] ±0.30°.

Further, according to the present invention, if present in the synthesized form, the X-ray diffraction pattern further includes X-ray diffraction peaks as substantially illustrated in the following table,

| 2θ (°) [a] | d-spacing (Å) | Relative intensity ($I/I_0 \times 100$) |
|---|---|---|
| 6.87 | 12.88 ± 0.56 | m-s |
| 14.25 | 6.21 ± 0.13 | w-m |
| 18.67 | 4.75 ± 0.08 | m-s |
| 19.71 | 4.50 ± 0.07 | w-m |
| 20.72 | 4.28 ± 0.06 | s |
| 21.60 | 4.11 ± 0.06 | m |
| 24.33 | 3.66 ± 0.04 | m |
| 25.21 | 3.53 ± 0.04 | m-s |
| 25.57 | 3.48 ± 0.04 | m |
| 26.12 | 3.41 ± 0.04 | m |
| 26.47 | 3.36 ± 0.04 | s |
| 27.62 | 3.23 ± 0.03 | w |

[a] ±0.30°.

According to the present invention, the SCM-11 molecular sieve has a specific surface area of 300-650 m²/g, preferably 350-550 m²/g.

According to the present invention, the SCM-11 molecular sieve has a micropore volume of 0.06-0.30 cm³/g, preferably 0.08-0.26 cm³/g, more preferably 0.10-0.24 cm³/g, more preferably 0.12-0.22 cm³/g, more preferably 0.14-0.20 cm³/g.

According to the present invention, the SCM-11 molecular sieve has a ring channel in the range of from 8-membered ring to 14-membered ring, preferably in the range of from 10-membered ring to 12-membered ring.

According to the present invention, the SCM-11 molecular sieve has a pore size (by the Argon adsorption method) of 0.54-0.80 nm, preferably 0.58-0.74 nm.

According to the present invention, there are significant signal peaks at the wave number of 384±10 and at the wave number of 487±10 in the UV Raman spectroscopy of the SCM-11 molecular sieve.

According to the present invention, the SCM-11 molecular sieve can be produced in line with the following process. In view of this, the present invention further relates to a process for producing the SCM-11 molecular sieve. The process includes a step of contacting under multiple step crystallization conditions a first oxide source, a second oxide source, an organic template, a fluorine source and water, to obtain a molecular sieve (referred to as the crystallization step).

According to the present invention, the multiple step crystallization conditions at least include: crystallizating at 80-110 degrees Celsius for 8 hours to 2 days, and then at 120-160 degrees Celsius for 1-10 days.

According to a preferred embodiment of the present invention, the multiple step crystallization conditions at least include: firstly crystallizing at 80-110 degrees Celsius for 12-36 hours, and then at 120-135 degrees Celsius for 4-36 hours, finally at 140-160 degrees Celsius for 1-7 days, more preferably firstly crystallizing at 90-110 degrees Celsius for 12-36 hours, and then at 125-135 degrees Celsius for 4-36 hours, finally at 140-155 degrees Celsius for 1-5 days, more preferably firstly crystallizing at 110 degrees Celsius for 18-30 hours, and then at 130 degrees Celsius for 12-36 hours, finally at 150 degrees Celsius for 1.5-3 days.

According to the present invention, in the process for producing the molecular sieve, each crystallization step of the multiple step crystallization may be conducted in any way known in this field, specifically there may be exemplified a way of hydrothermally crystallizing the corresponding mixture of each crystallization step under the corresponding crystallization conditions.

According to the present invention, in the process for producing the molecular sieve, the first oxide source is a silicon source.

According to the present invention, in the process for producing the molecular sieve, the second oxide source is at least two selected from the group consisting of a germanium source, an aluminum source, a boron source, an iron source, a gallium source, a titanium source, a rare earth source, an indium source and a vanadium source, more preferably a combination of a germanium source and at least one selected from the group consisting of an aluminum source, a boron source, an iron source, a gallium source, a titanium source, a rare earth source, an indium source and a vanadium source, more preferably a combination of a germanium source and at least one selected from the group consisting of an aluminum source, a boron source, a titanium source and a vanadium source, more preferably a combination of the germanium source and the aluminum source.

According to one embodiment of the present invention, generally speaking, for the second oxide source, if multiple oxide sources are used in combination, the ratio by molar between each two oxide sources is generally 1-99.6:99-0.4, preferably 33-99.5:67-0.5, more preferably 50-99:50-1, more preferably 60-99:40-1, more preferably 66-98:34-2, more preferably 66-97:34-3. Especially, if the second oxide source is a combination of the germanium source and the aluminum source, preferably Ge/Al=0.5-100, more preferably 1-50, more preferably 1.5-30, more preferably 2-20.

According to the present invention, in the process for producing the molecular sieve, as the first oxide source and the second oxide source, any corresponding oxide source known in this field for this purpose can be used, including but not limiting to the oxides, alkoxides, oxometallates, acetates, oxalates, ammonium salts, sulfates and nitrates of the corresponding metal in the oxide source. More specifically, as the silicon source, there may be exemplified silicic acid, silica gel, silica sol, tetralkoxysilane or water glass. As the germanium source, there may be exemplified tetralkoxy germanium, germanium dioxide, germanium nitrate. As the aluminum source, there may be exemplified aluminum hydroxide, sodium aluminate, aluminum salts, aluminum alkoxides, kaolin or montmorillonite. As aluminum salts, there may be exemplified aluminum sulfate, aluminum nitrate, aluminum carbonate, aluminum phosphate, aluminum chloride or alum. As aluminum alkoxides, there may be exemplified aluminum isopropoxide, aluminum ethoxide, aluminum butoxide. As the boron source, there may be exemplified boric acid, borate salt, borax, diboron trioxide. As the iron source, there may be exemplified ferric nitrate, ferric chloride, iron oxide. As the gallium source, there may be exemplified gallium nitrate, gallium sulfate, gallium oxide. As the titanium source, there may be exemplified titanium tetralkoxide, titania, titanium nitrate. As the rare earth source, there may be exemplified lanthanum oxide, neodymium oxide, yttrium oxide, cerium oxide, lanthanum nitrate, neodymium nitrate, yttrium nitrate, ceric ammonium sulfate. As the indium source, there may be exemplified indium chloride, indium nitrate, indium oxide. As the vanadium source, there may be exemplified vanadium chloride, ammonium metavanadate, sodium vanadate, vanadium dioxide, vanadyl sulfate.

According to one embodiment of the present invention, the second oxide source is at least one selected from the group consisting of germanium dioxide, boric acid, boron oxide, sodium metaborate, aluminum hydroxide, sodium aluminate, aluminum salts, kaolin, montmorillonite, tetra-n-butyl titanate, titanium tetrachloride, preferably at least two selected from the group consisting of germanium dioxide, boric acid, boron oxide, sodium metaborate, aluminum hydroxide, sodium aluminate, aluminum salts, aluminum alkoxides, kaolin, montmorillonite, tetra-n-butyl titanate, and titanium tetrachloride, more preferably a combination of germanium dioxide and at least one selected from the group consisting of boric acid, boron oxide, sodium metaborate, aluminum hydroxide, sodium aluminate, aluminum salts, kaolin, montmorillonite, tetra-n-butyl titanate, and titanium tetrachloride, more preferably a combination of germanium dioxide and at least one selected from the group consisting of boric acid, boron oxide, sodium metaborate, aluminum hydroxide, sodium aluminate, aluminum salts, and tetra-n-butyl titanate, more preferably a combination of germanium dioxide and at least one selected from the group consisting of boric acid, aluminum hydroxide, sodium aluminate, and aluminum salts, more preferably a combination of germanium dioxide and at least one selected from the group consisting of aluminum hydroxide, sodium aluminate, and aluminum salts.

According to the present invention, in the process for producing the molecular sieve, as the fluorine source, there may be exemplified fluoride or an aqueous solution thereof, especially HF.

According to the present invention, in the process for producing the molecular sieve, the organic template may be a compound represented by the following formula (A), a quaternary ammonium salt thereof or a quaternary ammonium hydroxide thereof, preferably 4-dimethylamino pyridine.

(A)

According to the present invention, in the formula (A), wherein $R_1$ and $R_2$ may be identical to or different from each other, each independently representing a $C_{1-8}$ alkyl, preferably a $C_{1-4}$ alkyl, more preferably a $C_{1-2}$ alkyl, most preferably both methyl.

According to the present invention, as the quaternary ammonium salt of the compound represented by the formula (A), there may be exemplified a quaternary nitrogen ($N^+$) structure obtained by additionally bonding a $C_{1-8}$ alkyl (preferably a $C_{1-4}$ alkyl, more preferably a $C_{1-2}$ alkyl or methyl) to the N atom in addition to the groups $R_1$ and $R_2$. As the counterion of the quaternary nitrogen, there may be exemplified a halo ion like $Br^-$, but not limiting thereto.

According to the present invention, as the quaternary ammonium hydroxide of the compound represented by the formula (A), there may be exemplified a quaternary nitrogen ($N^+$) structure obtained by additionally bonding a $C_{1-8}$ alkyl (preferably a $C_{1-4}$ alkyl, more preferably a $C_{1-2}$ alkyl or methyl) to the N atom in addition to the groups $R_1$ and $R_2$. As the counterion of the quaternary nitrogen, a hydroxyl ion ($OH^-$) is needed.

According to the present invention, in the process for producing the molecular sieve, the ratio by molar between the first oxide source (as the first oxide), the second oxide source (as the second oxide), the organic template, the fluorine source (as F) and water is 1:(0-0.5):(0.1-2.0):(0.1-2.0):(4-50), preferably 1:(0.001-⅓):(0.1-1.0):(0.1-1.0):(4-40), more preferably 1:(0.0025-0.25):(0.1-0.8):(0.1-1.0):(4-40), more preferably 1:(0.01-0.2):(0.1-0.6):(0.1-1.0):(5-30), more preferably 1:(0.02-0.2):(0.1-0.6):(0.1-1.0):(5-30).

According to the present invention, in the process for producing the molecular sieve, upon completion of all crystallization steps of the present multiple step crystallization, any separation method conventionally known in this field may be used to isolate a molecular sieve from the obtained reaction mixture as the final product, whereby obtaining the molecular sieve of the present invention. As the separation method, there may be exemplified a method wherein the obtained reaction mixture is filtered, washed and dried. Herein, filtering, washing and drying can be conducted in any manner conventionally known in this field. Specifically, as the filtration, there may be exemplified a method of simply suction filtering the obtained reaction mixture. As the washing, there may be exemplified a method of washing with deionized water. As the drying temperature, there may be exemplified a temperature of 40-250 degrees Celsius, preferably a temperature of 60-150 degrees Celsius, as the drying duration, there may be exemplified a duration of 8-30 h, preferably a duration of 10-20 h. The drying could be conducted under the normal pressure or a reduced pressure.

According to this invention, in the process, if needed, the obtained molecular sieve could be calcinated so as to remove the organic template and any water therefrom, whereby obtaining a calcinated molecular sieve (i.e. the molecular sieve in the calcined form), which corresponds to the molecular sieve of the present invention as well. The calcination could be conducted in any manner conventionally known in this field, for example, the calcination temperature is generally 300-800 degrees Celsius, preferably 400-650 degrees Celsius, while the calcination duration is generally 1-10 h, preferably 3-6 h. Further, the calcination is generally conducted under an oxygen containing atmosphere, for example, under the air atmosphere or under oxygen atmosphere According to the present invention, the obtained molecular sieves may be used in any physical form, for example, powder, particulate or a molded product (for example, strip, clover). These physical forms can be obtained in any manner conventionally known in this field, without any specific limitation thereto.

The SCM-11 molecular sieve according to this invention may be combined with other material, whereby obtaining a molecular sieve composition. As these other materials, there may be exemplified an active material and a non-active material. As the active material, there may be exemplified synthesized zeolites and natural zeolites, as the non-active material (generally referred to as binder), there may be exemplified clay, white earth, silica gel and alumina. As these other materials, one kind or a mixture of two or more kinds at any ratio therebetween could be used. As the amount of these other materials, any amount conventional used in this field could be used, without any specific limitation thereto.

The molecular sieve or the molecular sieve composition of the present invention can be used as an adsorbent, for example, that to be used in a gaseous or liquid phase to isolate at least one component from a mixture made of multiple components. In this way, a part of or substantially all of the at least one component can be isolated from the mixture. Specifically there may be exemplified a way wherein the molecular sieve or the molecular sieve composition is made to contact the mixture, whereby selectively adsorbing this component.

The molecular sieve or the molecular sieve composition of the present invention may be directly or after treated or converted (for example after ion exchanged) in a way conventionally used in this field regarding a molecular sieve used as a catalyst for converting an organic compound (or as a catalytic active component thereof). Specifically, according to the present invention, for example, reactants can be made to conduct a predetermined reaction in the presence of the catalyst for converting an organic compound to obtain the aimed product. As the predetermined reaction, there may be exemplified isomerization of normal paraffins, liquid phase alkylation between benzene and ethylene to produce ethyl benzene, liquid phase alkylation between benzene and propene to produce iso-propyl benzene, butene isomerization, naphtha cracking reaction, alkylation of benzene with ethanol, cyclohexenen hydration, toluene disproportionation to produce p-xylene, alkylation of toluene with methanol to produce p-xylene or disproportionation of iso-propyl naphthalene to produce 2,6-di(iso-propyl) naphthalene. In view of this, as the catalyst for converting an organic compound, there may be exemplified an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst or an aromatic disproportionation catalyst.

EXAMPLE

The following examples illustrate rather than limit this invention.

Example 1

3.6 g deionized water, 3.665 g of the organic template 4-dimethylamino pyridine, 1.046 g germanium dioxide, 0.378 g aluminum hydroxide, 7.5 g silica sol (containing $SiO_2$ 40 wt %), 1.501 g HF were mixed till homogeneous, to obtain a mixture with a ratio (ratio by molar) of:

$SiO_2/GeO_2=5$ $(SiO_2+GeO_2)/Al_2O_3=25$ 4-dimethylamino pyridine/$SiO_2$=0.6

$F/SiO_2$=0.6

$H_2O/SiO_2$=10 and then charged into a stainless steel reactor, under stirring firstly crystallized at 100 degrees Celsius for 24 hours, and then at 125 degrees Celsius for 24 hours, finally at 150 degrees Celsius for 5 days, upon completion of the crystallization, filtered, washed, dried at 110 degrees Celsius, calcined at 550 degrees Celsius in air for 6 hours to obtain a molecular sieve.

Figure 1:
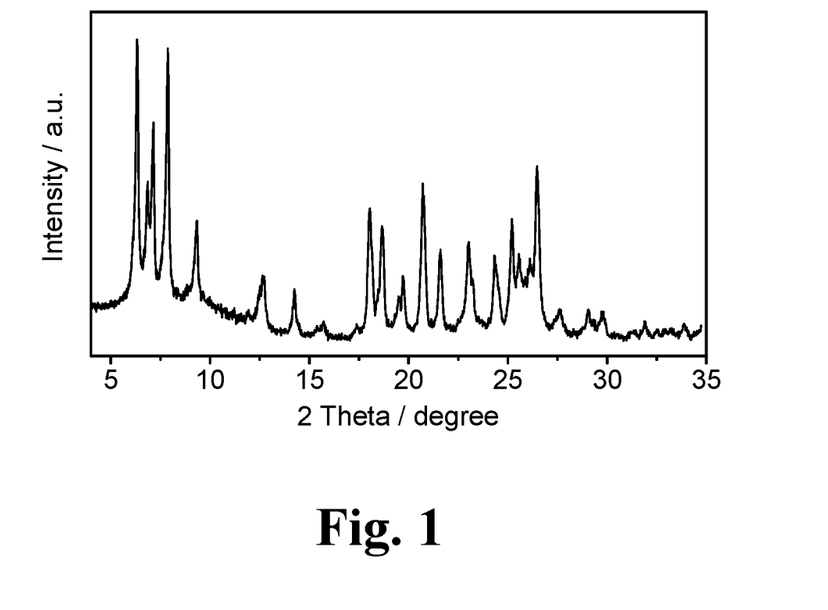
FIG. 1 illustrates the X-ray diffraction pattern (XRD) of the molecular sieve produced in Example 1 in the synthesized form.

The XRD data of the resultant molecular sieve (after dried at 110 degrees Celsius) were listed in Table 1, and the XRD pattern thereof was as illustrated in FIG. 1,

TABLE 1

| $2\theta/°$ | d/Å | $I/I_0 \times 100$ |
|---|---|---|
| 6.321 | 13.9718 | 100 |
| 6.867 | 12.8614 | 39.8 |
| 7.143 | 12.3647 | 60.3 |
| 7.877 | 11.2151 | 94.9 |
| 8.834 | 10.0018 | 4.9 |
| 9.334 | 9.4667 | 32.6 |
| 11.942 | 7.4048 | 4.3 |
| 12.633 | 7.0015 | 19.8 |
| 14.248 | 6.2109 | 17.7 |
| 15.39 | 5.7525 | 3.7 |
| 15.724 | 5.6313 | 5.5 |
| 17.383 | 5.0973 | 3.3 |
| 18.052 | 4.9099 | 49.4 |
| 18.665 | 4.7501 | 40.5 |
| 19.495 | 4.5495 | 12.1 |
| 19.713 | 4.4998 | 20.6 |
| 20.716 | 4.2842 | 57.9 |
| 21.602 | 4.1104 | 30.8 |
| 23.022 | 3.86 | 34.4 |
| 24.327 | 3.6558 | 27.6 |
| 25.211 | 3.5295 | 41.5 |
| 25.567 | 3.4812 | 27.3 |
| 26.119 | 3.4089 | 27.6 |
| 26.473 | 3.364 | 65.1 |
| 27.618 | 3.2272 | 8.3 |
| 29.075 | 3.0686 | 10 |
| 29.804 | 2.9952 | 7.6 |
| 31.342 | 2.8517 | 2.4 |
| 31.879 | 2.8048 | 6.1 |
| 33.249 | 2.6924 | 3.5 |
| 33.87 | 2.6444 | 4.9 |
| 34.897 | 2.5689 | 6.2 |
| 35.487 | 2.5275 | 6.6 |
| 37.078 | 2.4227 | 3.5 |
| 38.069 | 2.3618 | 6.7 |
| 38.504 | 2.3361 | 3.9 |

Figure 2:
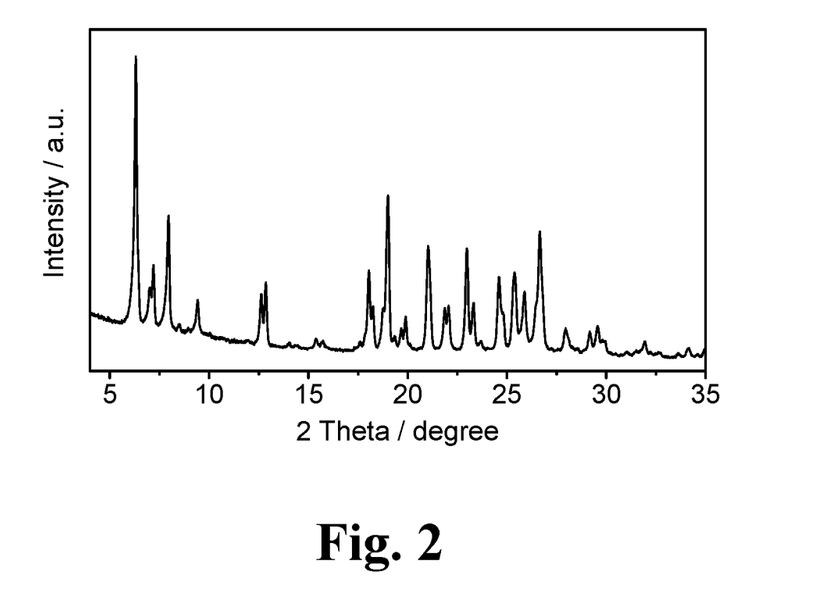
FIG. 2 illustrates the X-ray diffraction pattern (XRD) of the molecular sieve produced in Example 1 in the calcined form.

The XRD data of the resultant molecular sieve (after calcined at 550 degrees Celsius) were listed in Table 2, and the XRD pattern thereof was as illustrated in FIG. 2.

TABLE 2

| $2\theta/°$ | d/Å | $I/I_0 \times 100$ |
|---|---|---|
| 6.314 | 13.9865 | 100 |
| 7.001 | 12.6158 | 12.8 |
| 7.199 | 12.2695 | 21.7 |
| 7.965 | 11.0909 | 42.1 |
| 8.517 | 10.3734 | 2.4 |
| 8.952 | 9.8698 | 1.8 |
| 9.434 | 9.3666 | 13.1 |
| 11.971 | 7.3866 | 1 |
| 12.627 | 7.0044 | 18.9 |
| 12.86 | 6.878 | 23.6 |
| 14.047 | 6.2995 | 1.9 |
| 14.462 | 6.1198 | 1.1 |
| 15.383 | 5.7553 | 3.9 |
| 15.733 | 5.6281 | 3.3 |
| 17.602 | 5.0343 | 2.6 |
| 18.053 | 4.9096 | 29.1 |
| 18.268 | 4.8524 | 15.4 |
| 19.006 | 4.6656 | 56.7 |
| 19.341 | 4.5856 | 4.4 |
| 19.675 | 4.5083 | 6.6 |
| 19.906 | 4.4566 | 11.4 |
| 21.027 | 4.2214 | 38.8 |
| 22.062 | 4.0258 | 16.3 |
| 22.981 | 3.8668 | 37.9 |
| 23.329 | 3.8099 | 17.4 |
| 23.683 | 3.7537 | 2.9 |
| 24.601 | 3.6157 | 26.4 |
| 25.385 | 3.5057 | 26.9 |
| 25.886 | 3.4391 | 18.8 |
| 26.654 | 3.3416 | 42.7 |
| 27.957 | 3.1888 | 8.6 |
| 28.544 | 3.1245 | 1.4 |
| 29.176 | 3.0583 | 7.9 |
| 29.576 | 3.0178 | 10.5 |
| 29.911 | 2.9848 | 4.6 |
| 31.046 | 2.8782 | 1.4 |
| 31.513 | 2.8366 | 1.8 |
| 31.962 | 2.7977 | 5.3 |
| 32.649 | 2.7405 | 1.2 |
| 33.621 | 2.6634 | 1.3 |
| 34.168 | 2.622 | 3.3 |
| 34.614 | 2.5893 | 1.1 |
| 34.988 | 2.5625 | 3 |
| 35.638 | 2.5171 | 8.3 |
| 36.239 | 2.4768 | 5.3 |
| 36.574 | 2.4548 | 1.1 |
| 37.276 | 2.4102 | 3.1 |
| 38.477 | 2.3377 | 3.9 |
| 39.21 | 2.2957 | 0.7 |
| 39.767 | 2.2648 | 1.4 |

The resultant molecular sieve (after calcined at 550 degrees Celsius) has a specific surface area of 427 m$^2$/g, a micropore volume 0.17 cm$^3$/g, and a pore size (by the Argon adsorption method) of 0.64 nm.

Figure 3:
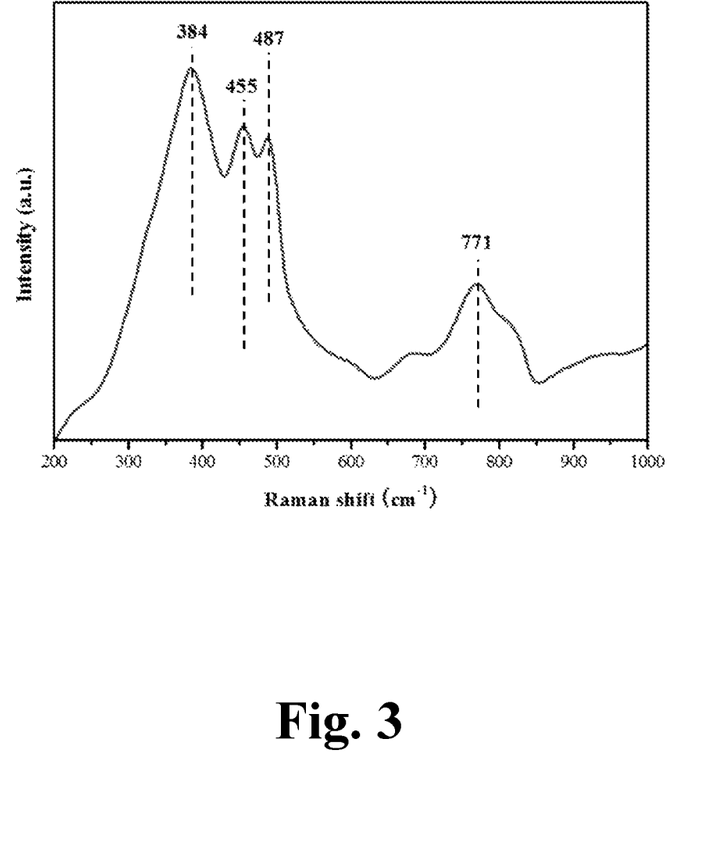
FIG. 3 illustrates the Raman spectra of the molecular sieve produced in Example 1 in the calcined form.

The resultant molecular sieve (after calcined at 550 degrees Celsius) has UV Raman spectroscopy as illustrated in FIG. 3, wherein there are significant signal peaks at the wave numbers of 384, 455, 487 and 771.

If determined by inductively coupled plasma-atomic emission spectroscopy (ICP), the sample after calcined has $SiO_2/GeO_2$=6.2, $(SiO_2+GeO_2)/Al_2O_3$=31.0.

Example 2

Similar to Example 1, except that $SiO_2/GeO_2$=10, $(SiO_2+GeO_2)/Al_2O_3$=30, 4-dimethylamino pyridine/$SiO_2$=0.8, $F/SiO_2$=0.3, $H_2O/SiO_2$=20, firstly crystallized at 100 degrees Celsius for 36 hours, and then at 145 degrees Celsius for 7 days.

The XRD data of the resultant molecular sieve (after dried at 110 degrees Celsius) were listed in Table 3 while the XRD pattern is similar to FIG. 1.

TABLE 3

| 2θ/° | d/Å | I/I₀ × 100 |
|---|---|---|
| 6.319 | 13.9766 | 85.5 |
| 6.853 | 12.8888 | 41.5 |
| 7.128 | 12.3908 | 28.6 |
| 7.876 | 11.2161 | 100 |
| 9.317 | 9.4847 | 30.6 |
| 12.63 | 7.0029 | 16.1 |
| 14.244 | 6.2128 | 14.5 |
| 15.411 | 5.745 | 3.7 |
| 15.727 | 5.6302 | 2.2 |
| 18.031 | 4.9155 | 36.8 |
| 18.683 | 4.7455 | 33 |
| 19.73 | 4.4959 | 22.3 |
| 20.734 | 4.2805 | 41.8 |
| 21.625 | 4.1061 | 23.7 |
| 23.003 | 3.863 | 27.1 |
| 24.382 | 3.6476 | 21.5 |
| 25.213 | 3.5292 | 30 |
| 25.565 | 3.4815 | 12.1 |
| 26.12 | 3.4088 | 7.7 |
| 26.455 | 3.3663 | 42.4 |
| 27.618 | 3.2272 | 6.9 |
| 29.056 | 3.0706 | 7.1 |
| 29.728 | 3.0028 | 5.9 |
| 31.225 | 2.8621 | 3 |
| 31.923 | 2.8011 | 4.2 |
| 32.504 | 2.7523 | 1.9 |
| 33.888 | 2.643 | 2.5 |
| 35.031 | 2.5594 | 3.7 |
| 35.467 | 2.5289 | 6.4 |
| 36.534 | 2.4575 | 2.7 |
| 36.925 | 2.4323 | 2.6 |
| 38.068 | 2.3619 | 5.4 |
| 38.678 | 2.326 | 3.7 |
| 39.758 | 2.2653 | 2 |

If determined by inductively coupled plasma-atomic emission spectroscopy (ICP), the sample after calcined has $SiO_2/GeO_2=11.5$, $(SiO_2+GeO_2)/Al_2O_3=37.2$.

Example 3

Similar to Example 1, except that $SiO_2/GeO_2=10$, $(SiO_2+GeO_2)/Al_2O_3=40$, 4-dimethylamino pyridine/$SiO_2=0.3$, F/$SiO_2=0.4$, $H_2O/SiO_2=25$, firstly crystallized at 110 degrees Celsius for 18 hours, and then at 145 degrees Celsius for 6 days.

The XRD data of the resultant molecular sieve (after dried at 110 degrees Celsius) were listed in Table 4 while the XRD pattern is similar to FIG. 1.

TABLE 4

| 2θ/° | d/Å | I/I₀ × 100 |
|---|---|---|
| 6.298 | 14.0225 | 37.1 |
| 6.869 | 12.8586 | 69.2 |
| 7.085 | 12.4656 | 53.7 |
| 7.878 | 11.2134 | 100 |
| 9.316 | 9.4855 | 29.4 |
| 10.305 | 8.5771 | 23.4 |
| 12.63 | 7.0028 | 18.6 |
| 14.265 | 6.2039 | 11.7 |
| 15.449 | 5.7308 | 13.7 |
| 15.686 | 5.6449 | 19.7 |
| 17.976 | 4.9306 | 31.4 |
| 18.588 | 4.7695 | 28.9 |
| 19.419 | 4.5673 | 10.7 |
| 19.731 | 4.4957 | 31.8 |
| 20.246 | 4.3825 | 8.3 |
| 20.696 | 4.2882 | 43.4 |
| 21.566 | 4.1172 | 18.4 |
| 22.944 | 3.8729 | 22.5 |
| 24.304 | 3.6592 | 24.5 |
| 25.192 | 3.5322 | 42.6 |
| 25.481 | 3.4927 | 19 |
| 26.024 | 3.4211 | 7.8 |
| 26.417 | 3.3711 | 40.5 |
| 27.559 | 3.234 | 10.3 |
| 28.919 | 3.0849 | 6.9 |
| 29.517 | 3.0237 | 10.5 |
| 31.186 | 2.8656 | 5.1 |
| 31.916 | 2.8017 | 7.4 |
| 34.755 | 2.5791 | 5.5 |
| 35.389 | 2.5343 | 9.7 |
| 36.406 | 2.4658 | 4.5 |
| 38.01 | 2.3654 | 9.2 |
| 38.506 | 2.336 | 5.2 |

If determined by inductively coupled plasma-atomic emission spectroscopy (ICP), the sample after calcined has $SiO_2/GeO_2=32.2$, $(SiO_2+GeO_2)/Al_2O_3=81.5$.

Example 4

Similar to Example 1, except that $SiO_2/GeO_2=7$, $(SiO_2+GeO_2)/Al_2O_3=15$, 4-dimethylamino pyridine/$SiO_2=0.2$, F/$SiO_2=0.25$, $H_2O/SiO_2=15$, firstly crystallized at 105 degrees Celsius for 30 hours, and then at 150 degrees Celsius for 5 days.

The XRD data of the resultant molecular sieve (after dried at 110 degrees Celsius) were listed in Table 5 while the XRD pattern is similar to FIG. 1.

TABLE 5

| 2θ/° | d/Å | I/I₀ × 100 |
|---|---|---|
| 6.301 | 14.0148 | 71.2 |
| 6.831 | 12.9283 | 45.4 |
| 7.128 | 12.3907 | 75.5 |
| 7.858 | 11.2411 | 100 |
| 9.298 | 9.5033 | 31.8 |
| 9.974 | 8.8608 | 3 |
| 10.434 | 8.4713 | 3.9 |
| 12.652 | 6.9908 | 15.6 |
| 14.229 | 6.2193 | 14.8 |
| 15.748 | 5.6227 | 9.9 |
| 17.371 | 5.1007 | 5 |
| 17.999 | 4.9243 | 40.6 |
| 18.649 | 4.7541 | 37.4 |
| 19.426 | 4.5656 | 7.5 |
| 19.733 | 4.4953 | 24.4 |
| 20.68 | 4.2915 | 46.7 |
| 21.57 | 4.1164 | 29.1 |
| 22.989 | 3.8655 | 28 |
| 23.521 | 3.7791 | 3.7 |
| 24.329 | 3.6555 | 24.7 |
| 25.178 | 3.5341 | 33.9 |
| 25.475 | 3.4936 | 12.7 |
| 26.067 | 3.4156 | 13.2 |
| 26.461 | 3.3655 | 49.2 |
| 27.605 | 3.2287 | 7.4 |
| 28.986 | 3.0779 | 7.9 |
| 29.714 | 3.0042 | 7.8 |
| 31.179 | 2.8662 | 2.7 |
| 31.922 | 2.8012 | 4.3 |
| 32.526 | 2.7506 | 1.5 |
| 33.246 | 2.6926 | 2.7 |
| 33.896 | 2.6425 | 3.9 |
| 34.803 | 2.5756 | 3.8 |
| 35.475 | 2.5283 | 5.9 |

TABLE 5-continued

| 2θ/° | d/Å | I/I₀ × 100 |
|---|---|---|
| 36.014 | 2.4917 | 4.8 |
| 36.878 | 2.4353 | 2.9 |
| 38.138 | 2.3577 | 7.9 |
| 39.678 | 2.2697 | 2.9 |

If determined by inductively coupled plasma-atomic emission spectroscopy (ICP), the sample after calcined has $SiO_2/GeO_2=9.5$, $(SiO_2+GeO_2)/Al_2O_3=18.2$.

Example 5

Similar to Example 1, except that $SiO_2/GeO_2=4$, $(SiO_2+GeO_2)/Al_2O_3=35$, 4-dimethylamino pyridine/$SiO_2=0.5$, $F/SiO_2=0.45$, $H_2O/SiO_2=15$, firstly crystallized at 110 degrees Celsius for 24 hours, and then at 130 degrees Celsius for 24 hours, finally at 150 degrees Celsius for 3 days. The XRD data of the resultant molecular sieve (after dried at 110 degrees Celsius) were listed in Table 6 while the XRD pattern is similar to FIG. 1.

TABLE 6

| 2θ/° | d/Å | I/I₀ × 100 |
|---|---|---|
| 6.299 | 14.02 | 71.2 |
| 6.814 | 12.9623 | 46.2 |
| 7.109 | 12.4244 | 77.2 |
| 7.855 | 11.2462 | 100 |
| 9.28 | 9.5217 | 33.6 |
| 12.615 | 7.0111 | 14.6 |
| 14.212 | 6.2269 | 14.6 |
| 15.632 | 5.6642 | 7.4 |
| 17.442 | 5.0801 | 4 |
| 17.998 | 4.9245 | 39.5 |
| 18.668 | 4.7493 | 38.5 |
| 19.444 | 4.5614 | 8 |
| 19.714 | 4.4995 | 19.3 |
| 20.681 | 4.2913 | 45.2 |
| 21.553 | 4.1197 | 27.4 |
| 22.988 | 3.8656 | 26 |
| 24.311 | 3.6582 | 21.7 |
| 25.16 | 3.5366 | 30.8 |
| 25.494 | 3.491 | 11.9 |
| 26.008 | 3.4231 | 18.3 |
| 26.461 | 3.3655 | 44.1 |
| 27.624 | 3.2265 | 7.9 |
| 29.006 | 3.0758 | 6.8 |
| 29.678 | 3.0077 | 4.9 |
| 30.521 | 2.9265 | 1.8 |
| 31.192 | 2.865 | 2.4 |
| 31.884 | 2.8044 | 4 |
| 32.486 | 2.7538 | 1.6 |
| 33.227 | 2.6941 | 2.6 |
| 33.84 | 2.6467 | 3.9 |
| 34.962 | 2.5642 | 3.7 |
| 35.496 | 2.5269 | 6.6 |
| 36.899 | 2.434 | 3 |
| 38.139 | 2.3577 | 5.4 |

If determined by inductively coupled plasma-atomic emission spectroscopy (ICP), the sample after calcined has $SiO_2/GeO_2=6.2$, $(SiO_2+GeO_2)/Al_2O_3=38.5$.

Example 6

Similar to Example 1, except that $SiO_2/GeO_2=3.5$, $(SiO_2+GeO_2)/Al_2O_3=15$, 4-dimethylamino pyridine/$SiO_2=0.7$, $F/SiO_2=0.7$, $H_2O/SiO_2=25$, firstly crystallized at 95 degrees Celsius for 36 hours, and then at 125 degrees Celsius for 1 days, finally at 155 degrees Celsius for 4 days.

The XRD data of the resultant molecular sieve (after dried at 110 degrees Celsius) were listed in Table 7 while the XRD pattern is similar to FIG. 1.

TABLE 7

| 2θ/° | d/Å | I/I₀ × 100 |
|---|---|---|
| 6.278 | 14.0674 | 69.6 |
| 6.792 | 13.0026 | 49.1 |
| 7.09 | 12.4567 | 79.2 |
| 7.82 | 11.2958 | 100 |
| 9.259 | 9.5433 | 34.4 |
| 9.951 | 8.8816 | 8.1 |
| 11.89 | 7.437 | 3 |
| 12.596 | 7.0217 | 13.5 |
| 14.191 | 6.2358 | 12.5 |
| 15.356 | 5.7655 | 3.6 |
| 15.711 | 5.6357 | 7.9 |
| 17.387 | 5.0963 | 4 |
| 17.977 | 4.9301 | 35.9 |
| 18.629 | 4.7592 | 38.1 |
| 19.438 | 4.5628 | 8.9 |
| 19.693 | 4.5043 | 17.8 |
| 20.661 | 4.2955 | 45.2 |
| 21.154 | 4.1964 | 4.9 |
| 21.55 | 4.1203 | 31 |
| 22.968 | 3.8689 | 26.2 |
| 24.273 | 3.6638 | 24.1 |
| 25.14 | 3.5394 | 32.6 |
| 25.456 | 3.4961 | 13.4 |
| 25.989 | 3.4256 | 22.4 |
| 26.44 | 3.3682 | 42.3 |
| 27.526 | 3.2377 | 6.9 |
| 29.003 | 3.0762 | 7.2 |
| 29.677 | 3.0078 | 6 |
| 31.194 | 2.8648 | 2.4 |
| 31.808 | 2.8109 | 4.6 |
| 32.475 | 2.7547 | 1.9 |
| 33.19 | 2.6971 | 2.5 |
| 33.816 | 2.6485 | 3.6 |
| 34.863 | 2.5713 | 4.8 |
| 35.417 | 2.5324 | 6.5 |
| 36.132 | 2.4839 | 1.6 |
| 36.863 | 2.4363 | 2.5 |
| 38.039 | 2.3636 | 5.3 |
| 38.396 | 2.3425 | 4 |
| 39.183 | 2.2972 | 1.7 |
| 39.66 | 2.2707 | 2.4 |

If determined by inductively coupled plasma-atomic emission spectroscopy (ICP), the sample after calcined has $SiO_2/GeO_2=51.0$, $(SiO_2+GeO_2)/Al_2O_3=18.5$.

Example 7

Similar to Example 1, except that $SiO_2/GeO_2=8$, $(SiO_2+GeO_2)/Al_2O_3=40$, 4-dimethylamino pyridine/$SiO_2=0.6$, $F/SiO_2=0.8$, $H_2O/SiO_2=30$, firstly crystallized at 95 degrees Celsius for 36 hours, and then at 155 degrees Celsius for 5 days.

The XRD data of the resultant molecular sieve (after dried at 110 degrees Celsius) were listed in Table 8 while the XRD pattern is similar to FIG. 1.

TABLE 8

| 2θ/° | d/Å | I/I₀ × 100 |
|---|---|---|
| 6.337 | 13.9357 | 100 |
| 6.854 | 12.8855 | 32.4 |
| 7.144 | 12.3639 | 91.3 |
| 7.876 | 11.2154 | 64.1 |
| 8.863 | 9.9691 | 7.4 |
| 9.335 | 9.4663 | 29.3 |
| 12.687 | 6.9717 | 14.6 |

TABLE 8-continued

| 2θ/° | d/Å | I/I₀ × 100 |
|---|---|---|
| 14.246 | 6.2118 | 9.4 |
| 15.685 | 5.645 | 7.1 |
| 17.498 | 5.0641 | 4.4 |
| 18.034 | 4.9149 | 38.7 |
| 18.704 | 4.7401 | 33.4 |
| 19.528 | 4.542 | 13 |
| 19.731 | 4.4956 | 13.2 |
| 20.791 | 4.2688 | 38.3 |
| 21.638 | 4.1035 | 24.8 |
| 23.12 | 3.8439 | 23.8 |
| 24.401 | 3.6448 | 19.3 |
| 25.211 | 3.5296 | 22.7 |
| 25.504 | 3.4896 | 11.3 |
| 25.783 | 3.4525 | 20.7 |
| 26.105 | 3.4107 | 7.9 |
| 26.512 | 3.3592 | 41.4 |
| 27.64 | 3.2246 | 7.3 |
| 29.035 | 3.0728 | 7.8 |
| 29.766 | 2.999 | 9.3 |
| 31.171 | 2.867 | 4.3 |
| 31.926 | 2.8009 | 4.1 |
| 33.909 | 2.6414 | 5.3 |
| 35.035 | 2.5591 | 4.2 |
| 35.502 | 2.5265 | 4 |
| 36.901 | 2.4338 | 3.4 |
| 38.261 | 2.3504 | 5.9 |
| 38.662 | 2.327 | 3.6 |
| 39.307 | 2.2903 | 3.5 |
| 39.812 | 2.2623 | 3 |

If determined by inductively coupled plasma-atomic emission spectroscopy (ICP), the sample after calcined has $SiO_2/GeO_2=81.0$, $(SiO_2+GeO_2)/Al_2O_3=39.5$.

Example 8

Similar to Example 1, except that $SiO_2/GeO_2=10$, $(SiO_2+GeO_2)/Al_2O_3=35$, 4-dimethylamino pyridine/$SiO_2=0.6$, $F/SiO_2=0.8$, $H_2O/SiO_2=30$, firstly crystallized at 105 degrees Celsius for 36 hours, and then at 115 degrees Celsius for 1 days, finally at 150 degrees Celsius for 6 days.

The XRD data of the resultant molecular sieve (after dried at 110 degrees Celsius) were listed in Table 9 while the XRD pattern is similar to FIG. 1.

TABLE 9

| 2θ/° | d/Å | I/I₀ × 100 |
|---|---|---|
| 6.318 | 13.9781 | 44.5 |
| 6.85 | 12.8936 | 39.2 |
| 7.141 | 12.368 | 15.1 |
| 7.877 | 11.2152 | 82 |
| 8.347 | 10.5846 | 100 |
| 8.897 | 9.9307 | 32.7 |
| 9.314 | 9.4875 | 16.2 |
| 9.932 | 8.898 | 23.5 |
| 12.647 | 6.9935 | 12.8 |
| 14.247 | 6.2114 | 10 |
| 15.398 | 5.7498 | 5.1 |
| 16.756 | 5.2867 | 5.3 |
| 17.423 | 5.0857 | 40.7 |
| 18.013 | 4.9203 | 26.3 |
| 18.349 | 4.831 | 44.5 |
| 18.646 | 4.7549 | 24.2 |
| 19.471 | 4.5551 | 44.6 |
| 19.709 | 4.5008 | 54.4 |
| 20.042 | 4.4266 | 10.6 |
| 20.698 | 4.2879 | 32.3 |
| 21.641 | 4.103 | 14.8 |
| 22.746 | 3.9061 | 48.2 |
| 23.022 | 3.86 | 28.8 |
| 24.521 | 3.6273 | 68 |
| 24.975 | 3.5624 | 72.6 |
| 25.707 | 3.4625 | 13.1 |
| 26.064 | 3.416 | 7.6 |
| 26.492 | 3.3617 | 43.8 |
| 27.771 | 3.2097 | 11.7 |
| 29.668 | 3.0087 | 12.2 |
| 30.334 | 2.9442 | 16.8 |
| 31.031 | 2.8796 | 11.2 |
| 32.093 | 2.7867 | 13.3 |
| 32.58 | 2.7461 | 6.5 |
| 33.215 | 2.6951 | 7.5 |
| 34.916 | 2.5675 | 8.5 |
| 35.519 | 2.5253 | 6.3 |
| 36.567 | 2.4553 | 7.5 |
| 37.278 | 2.4101 | 6.3 |
| 38.104 | 2.3597 | 6 |
| 38.701 | 2.3247 | 6.5 |

If determined by inductively coupled plasma-atomic emission spectroscopy (ICP), the sample after calcined has $SiO_2/GeO_2=95.0$, $(SiO_2+GeO_2)/Al_2O_3=271.2$.

Example 9

80 g of the molecular sieve produced in Example 3 in the form of powder was ion-exchanged by an aqueous ammonium nitrate solution (with a concentration of 1 mol/L) for 4 times, filtered, dried and then thoroughly mixed with 20 g alumina, introduced thereto a 5 wt % nitric acid solution and kneaded, molded by extrusion into φ1.6×2 mm strip, and then dried at 110 degrees Celsius, calcined at 500 degrees Celsius in air for 6 hours, whereby obtaining a desirable catalyst.

Example 10

80 g of the molecular sieve produced in Example 3 in the form of powder was ion-exchanged by an aqueous ammonium nitrate solution (with a concentration of 1 mol/L) for 4 times, filtered, and dried at 110 degrees Celsius, calcined at 500 degrees Celsius in air for 6 hours. Then, 1.5 g of the calcined molecular sieve was charged into a 100 ml stainless steel reactor, further introducing therein 35 g iso-propyl naphthalene, and closed the reactor. At 250° C., under 200 rpm stirring, the reaction was conducted for 6 hours. Upon completion of the reaction, the system was cooled to the room temperature, after centrifugally isolating the molecular sieve powder therefrom, the reaction product was analysed on an Agilent 19091N-236 gas chromatograph, indicating an iso-propyl naphthalene conversion of 32.28%, and a total selectivity to the aimed product 2,6-di(iso-propyl) naphthalene and 2,7-di(iso-propyl) naphthalene of 79.83%.

We claim:

1. An SCM-11 molecular sieve, having an empirical chemical composition as illustrated by the formula "the first oxide·the second oxide", wherein the first oxide is silica, the second oxide is a combination of germanium dioxide and at least one selected from the group consisting of alumina, boron oxide, iron oxide, gallium oxide, titanium oxide, rare earth oxides, indium oxide and vanadium oxide, a molar ratio of the first oxide to the second oxide is 3-1000, and the molecular sieve has X-ray diffraction pattern as substantially illustrated in the following table,

| 2θ (°) [a] | d-spacing (Å) | Relative intensity (I/I₀ × 100) |
|---|---|---|
| 6.31 | 13.99 | vs |
| 7.20 | 12.27 | w-m |
| 7.97 | 11.09 | m-s |
| 9.43 | 9.37 | w |
| 12.63 | 7.00 | w-m |
| 18.05 | 4.91 | m |
| 22.98 | 3.87 | m-s |

[a] ±0.30°.

2. The molecular sieve according to claim 1, wherein the X-ray diffraction pattern further includes X-ray diffraction peaks as substantially illustrated in the following table,

| 2θ (°) [a] | d-spacing (Å) | Relative intensity (I/I₀ × 100) |
|---|---|---|
| 12.86 | 6.88 | w-m |
| 18.27 | 4.85 | w |
| 19.01 | 4.67 | s |
| 19.91 | 4.46 | w |
| 21.03 | 4.22 | m-s |
| 22.06 | 4.03 | w |
| 23.33 | 3.81 | w |
| 24.60 | 3.62 | m |
| 25.39 | 3.51 | m |
| 25.89 | 3.44 | w-m |
| 26.65 | 3.34 | m-s |
| 27.96 | 3.19 | w |

[a] ±0.30°.

3. The molecular sieve according to claim 1, wherein the molecular sieve has a specific surface area of 300-650 m²/g and a micropore volume of 0.08-0.26 cm³/g.

4. The molecular sieve according to claim 1, wherein the molecular sieve has a ring channel in the range of from 8-membered ring to 14-membered ring, and a pore size (measured by the Argon adsorption method) of 0.54-0.80 nm.

5. The molecular sieve according to claim 1, having signal peaks at the wave number of 384±10 and at the wave number of 487±10 in the UV Raman spectroscopy thereof.

6. A molecular sieve composition, comprising the molecular sieve according to claim 1 and a binder.

7. A method of converting an organic compound, comprising contacting the organic compound with a catalyst comprising the molecular sieve according to claim 1.

8. The method of claim 7, wherein the catalyst is an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst, or an aromatic disproportionation catalyst.

9. A method of separating a component from a mixture, comprising contacting the mixture with an adsorbent comprising the molecular sieve of claim 1.

10. The molecular sieve according to claim 1, wherein the second oxide is a combination of germanium dioxide and alumina and the molar ratio of the first oxide to the second oxide satisfies $SiO_2/GeO_2>3$ and $(SiO_2+GeO_2)/Al_2O_3>5$.

11. An SCM-11 molecular sieve, in the synthesized form having an empirical chemical composition as illustrated by the formula "the first oxide·the second oxide·the organic template·water", wherein the first oxide is silica, the second oxide is a combination of germanium dioxide and at least one selected from the group consisting of alumina, boron oxide, iron oxide, gallium oxide, titanium oxide, rare earth oxides, indium oxide, and vanadium oxide, a molar ratio of the first oxide to the second oxide is 3-1000, a ratio by weight of the organic template to the first oxide is 0.05-0.33, a ratio by weight of water to the first oxide is 0-0.15, wherein the organic template is selected from a compound represented by the following formula (A), a quaternary ammonium salt thereof, and a quaternary ammonium hydroxide thereof, (A)

wherein $R_1$ and $R_2$ are identical to or different from each other, each independently representing a $C_{1-2}$ alkyl, and the molecular sieve has X-ray diffraction pattern as substantially illustrated in the following table,

| 2θ (°) [a] | d-spacing (Å) | Relative intensity (I/I₀ × 100) |
|---|---|---|
| 6.32 | 13.97 | vs |
| 7.14 | 12.36 | s |
| 7.88 | 11.22 | vs |
| 9.33 | 9.47 | m |
| 12.63 | 7.00 | w-m |
| 18.05 | 4.91 | m-s |
| 23.02 | 3.86 | m |

[a] ±0.30°.

12. The molecular sieve according to claim 11, wherein the X-ray diffraction pattern further includes X-ray diffraction peaks as substantially illustrated in the following table,

| 2θ (°) [a] | d-spacing (Å) | Relative intensity (I/I₀ × 100) |
|---|---|---|
| 6.87 | 12.86 | m-s |
| 14.25 | 6.21 | w-m |
| 18.67 | 4.75 | m-s |
| 19.71 | 4.50 | w-m |
| 20.72 | 4.28 | s |
| 21.60 | 4.11 | m |
| 24.33 | 3.66 | m |
| 25.21 | 3.53 | m-s |
| 25.57 | 3.48 | m |
| 26.12 | 3.41 | m |
| 26.47 | 3.36 | s |
| 27.62 | 3.23 | w |

[a] ±0.30°.

13. The molecular sieve according to claim 11, wherein the molecular sieve has a specific surface area of 300-650 m²/g, and a micropore volume of 0.08-0.26 cm³/g.

14. The molecular sieve according to claim 11, wherein the molecular sieve has a ring channel in the range of from 8-membered ring to 14-membered ring, and a pore size (measured by the Argon adsorption method) of 0.54-0.80 nm.

15. The molecular sieve according to claim 11, having signal peaks at the wave number of 384±10 and at the wave number of 487±10 in the UV Raman spectroscopy thereof.

16. The molecular sieve according to claim 11, wherein the second oxide is a combination of germanium dioxide and alumina and the molar ratio of the first oxide to the second oxide satisfies $SiO_2/GeO_2>3$ and $(SiO_2+GeO_2)/Al_2O_3>5$.

17. A process for producing an SCM-11 molecular sieve, comprising:
    a step of contacting, under multiple step crystallization conditions, a first oxide source,
    a second oxide source, an organic template, a fluorine source, and water, to obtain a molecular sieve, and optionally,
    a step of calcining the obtained molecular sieve,
    wherein the first oxide source is a silicon source, the second oxide source is a combination of the germanium source and the aluminum source,
    wherein the multiple step crystallization conditions comprise crystallizating at 80-110 degrees Celsius for 8 hours to 2 days, and then at 120-160 degrees Celsius for 1-10 days, and
    wherein the organic template is selected from a compound represented by the following formula (A), a quaternary ammonium salt thereof, and a quaternary ammonium hydroxide thereof, (A)

wherein $R_1$ and $R_2$ are identical to or different from each other, each independently representing a $C_{1-2}$ alkyl, and a molar ratio of the first oxide source (as the first oxide), the second oxide source (as the second oxide), the organic template, the fluorine source (as F), and water is $1:(0.001-\frac{1}{3}):(0.1-1.0):(0.1-1.0):(4-40)$.

18. The process according to claim 17, wherein the multiple step crystallization conditions comprise: firstly crystallizing at 80-110 degrees Celsius for 12-36 hours, and then at 120-135 degrees Celsius for 4-36 hours, finally at 140-160 degrees Celsius for 1-7 days.

19. The process according to claim 17, wherein the silicon source is at least one selected from the group consisting of silicic acid, silica gel, silica sol, tetralkoxysilane, and water glass, the germanium source is at least one selected from the group consisting of tetralkoxy germanium, germanium dioxide and germanium nitrate, the aluminum source is at least one selected from the group consisting of aluminum hydroxide, sodium aluminate, aluminum salts, aluminum alkoxides, kaolin and montmorillonite, the aluminum salts is at least one selected from the group consisting of aluminum sulfate, aluminum nitrate, aluminum carbonate, aluminum phosphate, aluminum chloride, and alum, the aluminum alkoxides is at least one selected from the group consisting of aluminum isopropoxide, aluminum ethoxide, and aluminum butoxide.

20. The process according to claim 17, wherein the molar ratio of the first oxide source (as the first oxide), the second oxide source (as the second oxide), the organic template, the fluorine source (as F) and water is $1:(0.0025-0.25):(0.1-0.8):(0.1-1.0):(4-40)$.

21. A molecular sieve composition, comprising the molecular sieve produced in line with the process according to claim 17, and a binder.

* * * * *